United States Patent
Valavanis

(10) Patent No.: US 11,779,435 B2
(45) Date of Patent: Oct. 10, 2023

(54) DENTAL SCREWDRIVER

(71) Applicant: Konstantinos Valavanis, Athens (GR)

(72) Inventor: Konstantinos Valavanis, Athens (GR)

(73) Assignee: FLEXSCREWDRIVER I.K.E., Maroussi (GR)

( * ) Notice: Subject to any disclaimer, the term of this patent is extended or adjusted under 35 U.S.C. 154(b) by 0 days.

(21) Appl. No.: 15/246,210

(22) Filed: Aug. 24, 2016

(65) Prior Publication Data

US 2017/0100205 A1    Apr. 13, 2017

Related U.S. Application Data

(60) Provisional application No. 62/210,346, filed on Aug. 26, 2015.

(51) Int. Cl.
  *B25B 23/00*  (2006.01)
  *B25B 13/48*  (2006.01)
  (Continued)

(52) U.S. Cl.
  CPC ............ *A61C 1/18* (2013.01); *A61B 17/8875* (2013.01); *A61B 90/92* (2016.02); *A61C 1/14* (2013.01);
  (Continued)

(58) Field of Classification Search
  CPC ........... A61C 1/18; A61C 1/14; A61C 8/0089; A61C 2201/007; A61C 3/00;
  (Continued)

(56) References Cited

U.S. PATENT DOCUMENTS 5,158,458 A * 10/1992 Perry ................... A61C 8/0089
                                                       433/141
5,464,407 A * 11/1995 McGuire ................ A61B 17/15
                                                       606/104
(Continued)

FOREIGN PATENT DOCUMENTS

CN        2806065 Y      8/2006
CN      101227871        7/2008
(Continued)

OTHER PUBLICATIONS

Nickel Titanium definition and material properties retrieved from https://en.wikipedia.org/wiki/Nickel_titanium (Year: 2021).*

(Continued)

*Primary Examiner* — Heidi M Eide
(74) *Attorney, Agent, or Firm* — DP IP GROUP; Franco S. De Liguori

(57) ABSTRACT

The disclosure relates to a dental screwdriver having a shaft portion made of a smart type alloy that bends with little or no resistance along an arch forming portion thereof and without imparting torqueing forces along a distal front end portion thereof onto which is connected a drive tip designed to interface with an appropriately sized screw. The smart alloy automatically assumes its original shape in the absence of twisting forces on the shaft along the arch forming portion. In an alternate embodiment, assuming the original shape involves applying heat and/or subtle finger pressure. The dental screwdriver may be part of a set of screwdrivers, each having a distal front end portion which is uniquely weighted, sized and/or dimensioned to accommodate different driver tips, handle different torqueing functions, and/or configured to bend to a specific maximum angular arch without permanent deformation. A dental prosthetic having a curved bore cavity is also described.

20 Claims, 11 Drawing Sheets

(51) Int. Cl.
<table>
<tr><td>A61B 17/88</td><td>(2006.01)</td></tr>
<tr><td>A61C 8/00</td><td>(2006.01)</td></tr>
<tr><td>A61B 17/00</td><td>(2006.01)</td></tr>
<tr><td>A61C 1/18</td><td>(2006.01)</td></tr>
<tr><td>A61B 90/92</td><td>(2016.01)</td></tr>
<tr><td>A61C 1/14</td><td>(2006.01)</td></tr>
<tr><td>A61B 90/00</td><td>(2016.01)</td></tr>
</table>

(52) U.S. Cl.
CPC .......... *A61C 8/0089* (2013.01); *B25B 13/481* (2013.01); *B25B 23/0021* (2013.01); *B25B 23/0028* (2013.01); *A61B 17/888* (2013.01); *A61B 2017/00464* (2013.01); *A61B 2017/00473* (2013.01); *A61B 2017/00862* (2013.01); *A61B 2017/00867* (2013.01); *A61B 2090/066* (2016.02); *A61C 8/0068* (2013.01); *A61C 2201/002* (2013.01); *A61C 2201/007* (2013.01)

(58) Field of Classification Search
CPC . A61B 17/8875; A61B 90/92; A61B 17/1631; B25B 15/001; B25B 15/002; B25B 17/00; B25B 19/00; F16C 1/02; F16C 23/6113
USPC ....... 433/141, 146, 147, 130, 173; 81/57.27, 81/177.6
See application file for complete search history.

(56) References Cited

U.S. PATENT DOCUMENTS

| | | | | |
|---|---|---|---|---|
| 5,597,378 A | * | 1/1997 | Jervis | A61F 2/01 606/78 |
| 5,807,241 A | * | 9/1998 | Heimberger | A61B 1/0055 600/139 |
| 6,450,815 B1 | * | 9/2002 | Weisman | A61C 13/30 433/220 |
| 6,575,747 B1 | * | 6/2003 | Riitano | A61C 5/42 433/102 |
| 7,648,599 B2 | * | 1/2010 | Berendt | C22F 1/10 148/563 |
| 9,039,415 B2 | * | 5/2015 | Streff | A61C 8/0048 433/173 |
| 9,744,008 B2 | * | 8/2017 | Bassett | A61C 8/0092 |
| 9,839,443 B2 | * | 12/2017 | Brockman | A61B 17/3478 |
| 2001/0024779 A1 | * | 9/2001 | Holweg | A61C 1/18 433/141 |
| 2002/0058551 A1 | * | 5/2002 | White | G06K 19/07 464/89 |
| 2007/0093840 A1 | * | 4/2007 | Pacelli | A61B 17/1631 606/80 |
| 2007/0161427 A1 | * | 7/2007 | White | F16C 1/02 464/52 |
| 2007/0218423 A1 | * | 9/2007 | Sapian | A61C 1/145 433/152 |
| 2007/0227314 A1 | * | 10/2007 | Erickson | B25B 23/142 81/467 |
| 2008/0140078 A1 | * | 6/2008 | Nelson | A61B 17/1615 606/80 |
| 2009/0306702 A1 | * | 12/2009 | Miloslavski | A61B 17/221 606/200 |
| 2010/0297583 A1 | * | 11/2010 | Benzon | A61C 8/0051 433/174 |
| 2011/0039229 A1 | * | 2/2011 | Senia | A61C 5/44 433/131 |
| 2012/0231414 A1 | * | 9/2012 | Johnson | B21K 5/02 433/102 |
| 2013/0261628 A1 | * | 10/2013 | Burley | A61B 17/1615 606/80 |
| 2014/0207233 A1 | * | 7/2014 | Steiner | A61F 2/0805 623/13.14 |
| 2014/0329197 A1 | * | 11/2014 | Bassett | A61C 8/0092 433/75 |
| 2015/0072311 A1 | * | 3/2015 | Benzon | A61C 13/08 433/202.1 |
| 2015/0374418 A1 | * | 12/2015 | Martin | A61B 17/1631 606/291 |
| 2016/0081772 A1 | * | 3/2016 | Schweiger | A61C 8/0048 433/173 |

FOREIGN PATENT DOCUMENTS

| | | | | |
|---|---|---|---|---|
| CN | 201524982 U | | 7/2010 | |
| CN | 202114721 | | 1/2012 | |
| CN | 103519910 | | 1/2014 | |
| CN | 103770088 A | | 5/2014 | |
| CN | 104114123 | | 10/2014 | |
| CN | 204308870 U | | 5/2015 | |
| CN | 204798043 | | 11/2015 | |
| EP | 1759658 | | 3/2007 | |
| EP | 2110097 B1 | | 10/2009 | |
| LI | 102013014660 A1 | * | 3/2015 | ........... A61C 8/0048 |
| WO | WO 2008/024062 | | 2/2008 | |
| WO | WO-2008024597 A2 | * | 2/2008 | ............ A61L 29/02 |
| WO | WO-2011080104 A1 | * | 7/2011 | ............ B25B 15/02 |
| WO | WO 2012/075551 | | 6/2012 | |
| WO | WO-2015032831 A1 | * | 3/2015 | ......... A61C 13/0022 |
| WO | WO 2018/037250 | | 3/2018 | |

OTHER PUBLICATIONS

PCT International Search Report (dated Oct. 19, 2017) of US counterpart.
International Preliminary Report on Patentability dated Mar. 7, 2019 From the International Bureau of WIPO Re. Application No. PCT/GR2017/000045. (10 Pages).
Notification of Office Action and Search Report dated Aug. 20, 2020 From the State Intellectual Property Office of the People's Republic of China Re. Application No. 201780065530.6 and Its Summary in English. (13 Pages).
Communication Pursuant to Article 94(3) EPC dated May 26, 2020 From the European Patent Office Re. Application No. 17761915.2. (6 Pages).
Communication Pursuant to Article 94(3) EPC dated Jun. 22, 2021 From the European Patent Office Re. Application No. 17761915.2. (8 Pages).
Search Report and Opinion dated Apr. 8, 2021 From the Servico Publico Federal, Ministerio da Economia, Instituto Nacional da Propriedade Industrial do Brasil Re. Application No. BR112019003751-9. (4 Pages).
Translation Dated Apr. 28, 2021 of Search Report and Opinion dated Apr. 8, 2021 From the Servico Publico Federal, Ministerio da Economia, Instituto Nacional da Propriedade Industrial do Brasil Re. Application No. BR112019003751-9. (4 Pages).
Notification of Office Action and Search Report dated May 27, 2021 From the China Intellectual Property Administration Re. Application No. 201780065530.6. (7 Pages).
Translation Dated Jun. 28, 2021 of Notification of Office Action dated May 27, 2021 From the China Intellectual Property Administration Re. Application No. 201780065530.6. (4 Pages).

* cited by examiner

DENTAL SCREWDRIVER

RELATED APPLICATIONS

The present application claims priority to related U.S. Provisional application 62/210,346 filed on Aug. 26, 2015, entitled "Dental Screwdriver", commonly owned and assigned herewith.

FIELD

The present disclosure relates to bendable screwdrivers, and in particular, to bendable screwdrivers for use in dentistry for securing screw-retained restorations and like-sized components.

BACKGROUND

A dental implant (also known as an endosseous implant or fixture) is a surgical component that interfaces with the bone of the jaw or skull to support a dental prosthesis such as a crown, bridge, denture, facial prosthesis or to act as an orthodontic anchor. The basis for modern dental implants is a biologic process called osseointegration where materials, such as titanium, form an intimate bond to bone. A variable amount of healing time is required for osseointegration before the dental prosthetic (a single crown, bridge or denture) is attached to the implant. Alternatively the dental prosthetic can be immediately attached to the implant before osseointegration has occurred for aesthetic and/or functional reasons.

Planning the position and number of implants is key to the long-term health of the prosthetic since biomechanical forces created during chewing can be significant. The position of implants is determined in large part by the position and angle of adjacent teeth.

The final prosthetic can be either fixed, where a person cannot remove the denture or teeth from their mouth or removable, where they can remove the prosthetic. In each case an abutment is necessary which couples the dental prosthetic to the implant.

The risks and complications related to implant therapy are divided into those that occur during surgery (such as excessive bleeding or nerve injury), those that occur in the first six months (such as infection and failure to osseointegrate) and those that occur long-term (such as peri-implantitis and mechanical failures). In the presence of healthy tissues, a well-integrated implant with appropriate biomechanical loads can have long term success rates of 93 to 98 percent for the fixture and 10 to 15 year lifespans for the prosthetic teeth.

The securing of screw-retained restorations is usually performed using appropriately sized and fitted screwdrivers. A screw-retained fixation is very often positioned at an angle in relation to the restoration's anterior plane.

Restorations having a non-straight or even a bended screw channel not only allow flexibility in designing screw retained crowns, bridges and/or dentures, they also eliminate the need for cementing restorations.

FIG. 1 is a cross-sectional view 10 of a conventional cemented type restoration. In a cemented type restoration, a dental implant 11 is first osseointegrated in the jaw portion 12 of a patient's mouth and then a traditional prosthetic abutment 15 is threadedly secured into the implant. Once the abutment is secured in position, the implant specialist cements the prosthetic over the abutment as shown.

The alternate, screw retained approach 20 is best shown and illustrated in FIGS. 2A and 2B. In this approach, the abutment is integral with the artificial crown, bridge or denture that's fitted into the patient. Instead of first inserting an abutment and then cementing a crown over the abutment, as for example is shown in FIG. 1, here the dental prosthetic (and integrated abutment) is positioned into the implant and secured using a screw. The prosthetic is provided with cavity that extends axially from an opening on the enameled surface of the prosthetic into and across the integrated abutment terminating into the implant's co-axial threaded cavity. To secure the prosthetic into the implant using a screw, the prosthetic cavity is sized to fit the screw and also the screwdriver shaft which must be able to reach and secure the screw to the implant.

In FIG. 2A, the restoration is shown just before the screw is inserted and secured.

In FIG. 2B, a screwdriver is shown extending into the prosthetic cavity with intent to reach the screw (not shown) used to threadedly secure the prosthetic from the implant. In a similar manner, the prosthetic can be removed by unscrewing the screw.

The screwdriver typically used with screw-retainer restorations are screwdrivers with non-bendable shafts. The tips of commercially available screwdrivers are sized to accommodate design specifications of one or more specific implant vendors.

Screwdrivers and screwdrivers tips come in varying sizes and shapes depending on the specifications and screw types called for by the restoration's manufacturer. Very often, different manufacturers intentionally size restorations to force practitioners to purchase a specific set of tools (including screwdrivers) which works in favor of the restoration manufacturers since practitioners are less likely to switch to a different manufacturer if doing so may require buying a new set of tools. With that said, over time, tools have been introduced with interchangeable heads and tips to address this problem.

Despite the overall benefits of such screw-retained restorations, there remain significant manufacturing and aesthetic limitations involved in creating a suitable restoration. This is partly attributed to the fact that in cases where the implant axis is going through the anterior plane of the restoration-prosthesis and due to the fact that the traditional dental screwdrivers do not allow any angulation during the securing (screwing) of the restoration, the screw channel must end buccally resulting in a less aesthetically satisfactory restoration.

One design approach for securing angled screw-retained restorations and implant abutments in particular is described in international patent application WO2011080141, filed on Dec. 16, 2010 and assigned to Straumann Holding AG (hereafter "Straumann") entitled "FLEXIBLE DENTAL SCREWDRIVER AND METHOD OF MANUFACTURING THE SAME".

FIGS. 3A-3C are different perspective views of a prior art Straumann screwdriver 55. The Straumann screwdriver 55 is capable of bending along the shaft region by virtue of a multitude of cylindrically shaped hollow shaft segments 60 that combine to form a flexible shaft 65. The flexible shaft segments interlock to provide limited movement in any direction along the shaft, substantially as shown in accompanying FIG. 3A.

FIGS. 3B and 3C are blown up, top level diagrammatic view and cross-sectional views, respectively, showing a single shaft segment 60. Due to the interlocking nature of segments 60 along shaft 65, a torque applied to shaft 65 from a handle portion 70 is transferred to a connected or integral drive tip 75. The dimensions of screwdriver 55, including size and number of shaft segments, depend on the amount of torque and desired range of curvature desired. In practice, however, the segmented nature of the Straumann design makes it impractical for all but the easiest-to-access restorations. The shaft is difficult to clean and costly to manufacture; difficult to apply even torque pressure along the vertical axis of the screw in many instances; and other inefficiencies.

A more recent approach in dealing with angled screwed restorations has been recently proposed by Nobel Biocare which employ a unique screw head which it calls an Omnigrip™ Interface design.

FIGS. 4A-4I illustrate the prior art Omnigrip approach.

Referring to FIG. 4A, this is a partial perspective view of a patient's mouth. One tooth is very clearly a screw-retained type restoration 405, given the presence of a bore cavity 406 which is shown in ghost view.

A cross-sectional view of restoration 405 is shown in FIG. 4B. Here, we see very clearly the presence of a dental prosthetic 410 fixed by as screw (not shown) threaded along a planar axis to a dental implant 420. An appropriate set of abutments connecting dental prosthetic 410 to dental implant 420, similar to the restoration shown in FIGS. 2A and 2B, while not shown may be presumed. The purpose of bore cavity 406 is to facilitate feeding a screwdriver into the open cavity to allow fixedly securing the appropriate screw.

In the configuration shown in FIG. 4B, dental prosthetic 410 is designed to be screwed at angle of 0 degrees off axis from the abutment face. Obviously, this has the negative result of providing ingress to cavity 406 from the front of the dental prosthetic. This means once the prosthetic is secured in place, the dental practitioner must fill the whole of the prosthetic (crown) to achieve a desired tooth-like aesthetic look and feel. This is not always easy or possible to achieve when a bore cavity is large.

An alternative approach to fix a dental prosthetic is to provide the bore cavity through which the screw will be secured at an angular level off axis. This way the opening of the bore cavity is not visible from the front. All the filling is done anteriorly.

An example cross-sectional view of a restoration 425 with a dental prosthetic 432 having an associated bore cavity positioned at an offset of 25 degrees off the planar axis of dental implant 433 is shown in FIG. 4C.

Referring to FIGS. 4D-4F, we see that for the restoration of FIG. 4D, a specially designed screw 435, screwdriver 440, and screwdriver tip interface 445 must be provided to facilitate angular torqueing (450) of screw 435 along the 25 degree axis off the anterior plane of dental implant 433 in the illustrated example.

For greater accuracy in providing proper torqueing to an optimal final setting, a torque adjusting tool 460 may be coupled to the screwdriver handle. An example of this is shown in shown in FIGS. 4H and 4I.

To allow the non-bendable type screwdriver 440, as shown, to reach the screw in order to fixedly secure dental prosthetic 432 into dental implant 433, it is necessary that the opening associated with bore cavity be large enough to permit positioning screwdriver therein at an angle. Often this is only possible if bore cavity is partially open or exposed.

The use of a Straumann type screwdriver very clearly is not suitable for a number of reasons. For one, it is not believed possible to guarantee that the Straumann screwdriver will apply the twisting forces imparted on the Straumann handle so as to generate the desired torqueing forces on the head of the screw in the same manner and to the same extent as a non-bendable screwdriver. Any off-planar axis, or like uneven forces, could result in improper threading and possible destruction of the dental implant, the dental prosthetic, the screw, associated abutments, or a combination of the above.

In addition, it is not believed possible to design a suitable Straumann screwdriver that will bend along its tip in an optimal manner so as to impart a perfectly vertical pushing force on the screw during threading.

Additionally, it is not clear that the Straumann screwdriver may be used with accuracy when employing a torque adjusting tool.

Regarding the Omnigrip approach, in addition to the need for a non-bendable screwdriver, as described above, it also suffers from a number of drawbacks which makes its use by practitioners difficult, costly, and inflexible in terms of being able to use the drive tips for other dental related functions, applications and/or with different manufacturer screw heads/tips.

There is a need therefore for an improved screwdriver design that is low cost, easy to use, efficient, flexible, versatile, robust, more hygiene-friendly, capable of preventing the incidence of peri-implantitis resulting from improper screwing, mechanically fail proof, and at the same time manufacturer tip- and screw-head agnostic.

SUMMARY

The present disclosure relates to a dental screwdriver having a shaft portion made of a smart type alloy that bends with little or no resistance along an arch forming portion thereof and without imparting torqueing forces along a distal front end portion thereof onto which is connected a drive tip designed to interface with an appropriately sized screw. The smart alloy automatically assumes its original shape in the absence of bending forces on the shaft along the arch forming portion. In an alternate embodiment, assuming the original shape involves applying heat and/or subtle finger pressure.

In accordance with a further exemplary embodiment, the dental screwdriver is part of a set of screwdrivers, each having a distal front end portion which is uniquely weighted, sized and/or dimensioned to accommodate different driver tips, handle different torqueing functions, and/or configured to bend to a specific maximum angular arch without permanent deformation. The screwdrivers may be uniquely identified (e.g., color coded) to identify the screwdriver's design specifications, such as elasticity type parameters.

In another embodiment, the set of screwdrivers are designed to have integral tips to accommodate different manufacturer screw heads.

In another embodiment, the shaft includes a second distal end, opposite the distal front end portion gripping end of the shaft, configured to couple to a handle portion, or to a torque measuring tool. The handle portion itself may also be designed to work with a conventional torque measuring tool.

In another embodiment, the smart alloy is sized and or made of smart alloy material along just that portion of the shaft intended to receive the optimum bending forces without imparting any bending action or force along the distal front end portion, which distal front end portion is made of either a non-smart alloy material, or of a smart alloy material of different type.

In yet another embodiment, the drive tips are sized with diameters less than or equal to 0.4 mm resulting in smaller vents (cavities) in the crown which results in increased overall strength of the restoration.

In a preferred embodiment, the smart alloy is Nickel titanium.

In an example scenario, the dental screwdriver is characterized by very high elasticity. Exposing the screwdriver to heating and/or applying subtle finger pressure helps with recovery to an original shape prior to bending. As such, the dental screwdriver is able to achieve a very high kink-resistance in concert with the ability to bend through torturous paths without experiencing strain localization and/or plastic deformation.

In yet another embodiment, the dental screwdriver has a very narrow design profile and sized to couple to an elastic abutment extractor or activator for Morse taper implant designs. This allows removing an abutment immediately after screw removal or, alternatively, to tighten an abutment without the use of a screw.

In yet another embodiment, the dental screwdriver is sized to have a very long shaft for flexibility in hard to reach places. The same shaft may alternatively include a telescopic portion disposed along a non-bendable, non-elastic portion of the shaft for even greater flexibility in use.

In yet a further embodiment, at least one of the shaft and the distal front end portion are magnetized to magnetically grip either a driver tip, the screw to be inserted, or both.

In yet a further embodiment there is further provided screws made of similar smart alloy material designed to conform to the specific shape of a vent or screw cavity when positioned for screwing to take advantage of the greater flexibility and reach the dental screwdriver proposed herein.

In yet a further embodiment, an electronic platform or stand-alone software tool is provided to facilitate in the training or appropriate selection of a screwdriver having an elasticity, size, and/or dimension matching a restoration's optimum design specifications.

In another aspect, a screw-retained type dental prosthetic is provided having a curved bore cavity configured to facilitate the use of a bendable screwdriver. The dental prosthetic includes an artificial tooth portion coupled to a prosthetic abutment. The curved bore cavity extends from an opening in the artificial tooth portion to an opening in the prosthetic abutment. The bendable screwdriver is a screwdriver of the type having a shaft made of a smart alloy with shape memory and superelasticity.

A method is also disclosed which involves identifying a screw type to be used to secure a dental prosthetic to a dental implant. At least one of a bendable screwdriver having a smart alloy shaft with integral drive tip end, a smart alloy shaft with integral drive tip end, and a drive tip end of the type configured to connect to a smart alloy shaft, are selected from a set of a plurality of same, respectively, on the basis of the screw type identified.

These and other features and advantages of the present invention will be apparent from the description of exemplary embodiments provided herein.

BRIEF DESCRIPTION OF THE DRAWINGS

Purposes and advantages of the exemplary embodiments will be apparent to those of ordinary skill in the art from the following detailed description in conjunction with the appended drawings in which like reference characters are used to indicate like elements, and in which.

DETAILED DESCRIPTION

The word "exemplary" is used herein to mean "serving as an example, instance, or illustration." Any embodiment described herein as "exemplary" is not necessarily to be construed as preferred or advantageous over other embodiments.

The following description is intended to convey a thorough understanding of the embodiments described by providing a number of specific embodiments and details involving methods and systems for managing content submission and publication of content. It should be appreciated, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments, depending upon specific design.

The terminology used herein is for the purpose of describing particular embodiments only and is not intended to limit the scope of the present invention. As used throughout this disclosure, the singular forms "a," "an," and "the" include plural reference unless the context clearly dictates otherwise. Thus, for example, a reference to "a module" includes a plurality of such modules, as well as a single module, and equivalents thereof known to those skilled in the art.

The present disclosure relates to a dental screwdriver having a shaft portion made of a smart type alloy that bends with little or no resistance along an arch forming portion thereof and without imparting torqueing forces along a distal front end portion thereof onto which is connected a drive tip designed to interface with an appropriately sized screw. The smart alloy automatically conforms to its original shape upon removal of the twisting forces on the shaft along the arch forming portion which caused the arching in the first place.

In an alternate embodiment, assuming the original shape involves applying heat and/or subtle finger pressure.

In accordance with a further exemplary embodiment, the dental screwdriver is part of a set of screwdrivers, each having a distal front end portion which is uniquely weighted, sized and/or dimensioned to accommodate different driver tips, handle different torqueing functions, and/or configured to bend to a specific maximum angular arch without permanent deformation. The screwdrivers may be uniquely identified (e.g., color coded) to identify the screwdriver's design specifications, such as elasticity type parameters.

In another embodiment, the set of screwdrivers are designed to have integral tips to accommodate different manufacturer screw heads.

Figure 5:
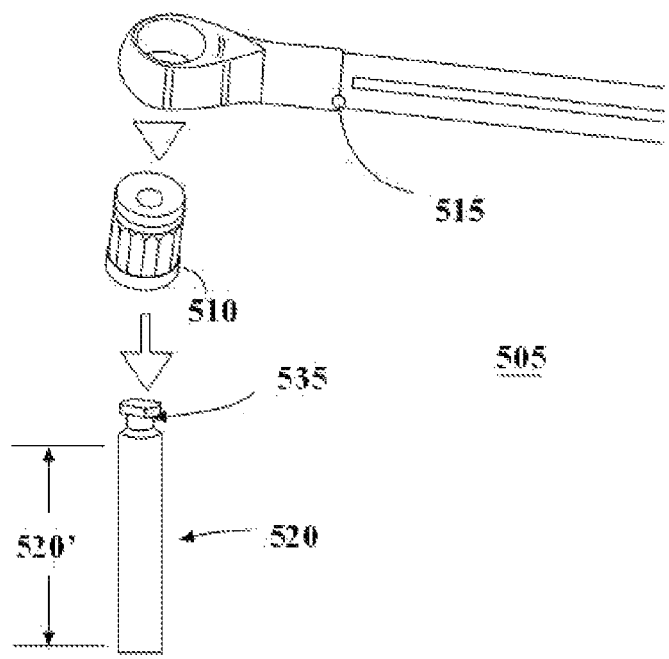
FIG. 5 is an example dental screwdriver in accordance with an exemplary embodiment with integral tip(s).
Figure 5:
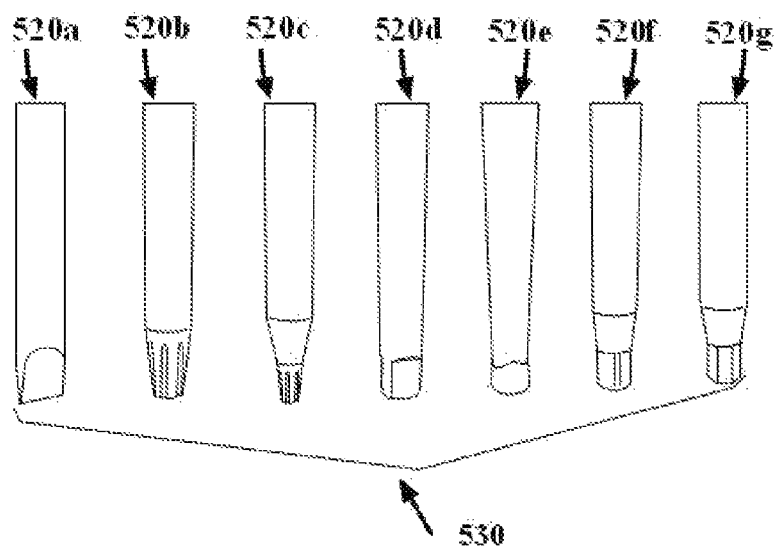

An example dental screwdriver 505 in accordance with an exemplary embodiment with integral tip(s) is shown in FIG. 5. The screwdriver 505 includes a handle portion 510 and a shaft 520, and designed to couple to any conventional torque measuring tool 515. As can be seen, a shaft 520 may be provided with any number of different integral driver tips (shown as shaft portions 520a-520g). Each of shaft portions 520a-520g are integrally formed and extend downwardly from a topmost shaft portion 520'. Shaft portions 520a-520g are a few examples of different integrated screwdriver tips with which shaft 520 may be designed/provided.

Screwdriver 505 may be marketed and sold as a stand-alone integral shaft made of a smart alloy material and provided with a specific driver tip, such as anyone or the driver tip options 520a-520g (collectively 530) shown in FIG. 5. In one scenario, a commercial offering may include an entire set of screwdriver shafts with different driver tips. In an alternate embodiment, the topmost shaft portion 520' comprises one part of shaft 520 which extends into a bendable smart alloy portion with the latter being adapted and sized to receive different types of driver tips. This way, a commercial offering comprises a set of rigid driver tips configured to be connected in any one of different known ways to a shaft comprised of smart alloy material. One skilled in the art would appreciate that there are many, many different tips and the decision to market a set of screwdrivers with more or fewer tips is a commercial decision.

Shaft 520, in accordance with an exemplary embodiment, includes a latch end 535 designed to mate and fixedly secure the shaft to handle portion 510, or directly to a torque measuring tool depending one type of mechanism design one chooses to employ.

The key aspect is the shaft construction and design. The shaft 520 may recover its shape after bending due to the use of smart alloy type material. Shape recovery may be automatic (e.g., no heating, electricity, or magnetism is applied). In another scenario, the recovery is assisted in that a minimum amount of finger pressure or some form of heat is involved for the smart alloy shaft to fully return to a non-bent position.

In a preferred embodiment, the smart alloy is Nickel titanium, also known as nitinol. Nitinol is a metal alloy of nickel and titanium, where the two elements are present in roughly equal atomic percentages e.g. Nitinol 55, Nitinol 60. Nitinol alloys exhibit two closely related and unique properties: shape memory and superelasticity.

Shape memory is the ability of nitinol to undergo deformation at one temperature, then recover its original, undeformed shape upon heating above its "transformation temperature". Superelasticity occurs at a narrow temperature range just above its transformation temperature. In the scenario where the shaft exhibits "superelasticity", no heating may be necessary to cause the undeformed shape to recover. The uniqueness of using a material like Nitinol is that it can, under certain uses, possess both shape memory and superelasticity. In uses where complete superelasticity is either not possible or not desirable, applying heat or some gentle finger pressure to assist with recovery into an unbent position may be necessary or desirable.

Applicants tap the special nature of Nitinol to construct a dental screwdriver which for the first time aims to allow dental practitioners to fit a screwdriver through closed bore cavity spaces, both curved and straight, through which the smart alloy shaft end will travel to reach a screw used to secure a dental prosthetic to a dental implant.

Due to the nature of the shaft being bendable, except at or near the point of impact between the shaft end and the screw, the twisting forces applied by the practitioner are evenly and uniformly transferred through the shaft as if the screwdriver shaft were a non-bendable type shaft.

In accordance with an exemplary embodiment, the smart alloy is sized and or made of smart alloy material along just that portion of the shaft intended to exhibit an optimum bending characteristic (elasticity) without imparting any bending action or force along the portion 520' of shaft 520 which extends from latch end 535.

In one scenario, portion 520' is made of either a non-smart alloy material, or of a smart alloy material of different elasticity, or of the same smart alloy but with different elasticity attributes along the shaft length to achieve desired bendability consistent with the intended action to be taken.

In yet another embodiment, the drive tips are sized with diameters less than or equal to 0.4 mm resulting in smaller vents (cavities) in the crown which results in increased overall strength of the restoration.

In yet a further embodiment, it is contemplated that the ability, for the first time, to be able to provide an accurate bendable screwdriver with tip ends that can fit along a curved bore cavity in a dental prosthetic which extends to a prosthetic abutment designed to receive a screw, gives rise to new type dental prosthetic devices (crowns, bridges, and the like) which may be constructed with curved bore cavities and designed to work with bendable, smart alloy shafted dental screwdrivers, as proposed herein.

Figure 6:
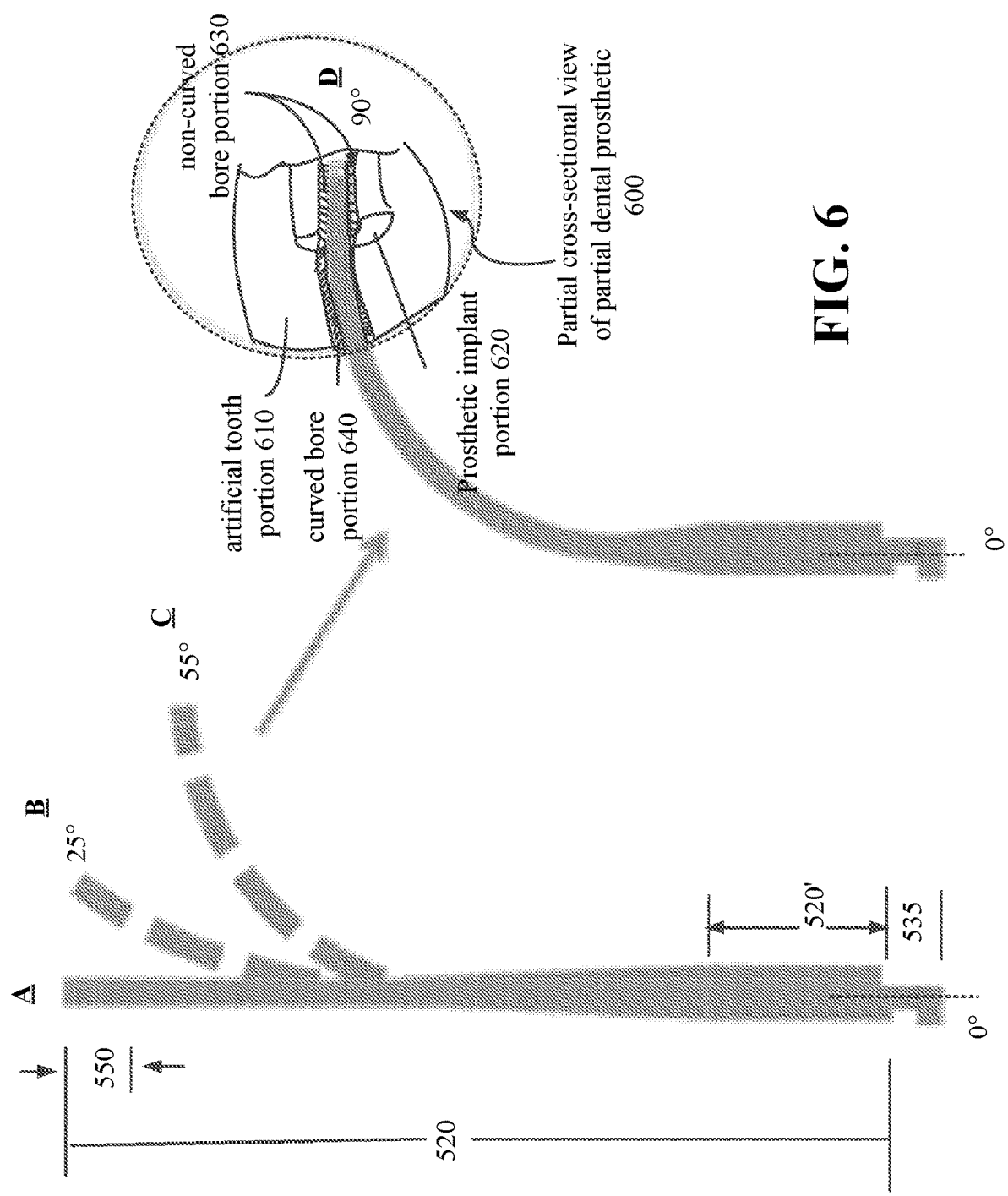
FIG. 6 is a graphical illustration of superelastic bending behavior of the proposed dental screwdriver manufactured from smart alloy material.

A graphical illustration of superelastic bending behavior of the proposed dental screwdriver manufactured with smart alloy material (preferably nitinol) is illustrated in FIG. 6.

Here we see shaft 520 bent to different angles. Latch end 535 and shaft portion 520' do not bend at all. By contrast, the smart alloyed portion of shaft 520 is designed to flexibly bend to different angles and with different degree of curvature depending on the bending force applied, as shown. In position A, shaft 520 is shown in a natural state (non-bent) position. In position B, we see shaft 520 bent at approximately 25 degrees off normal state (position A). In position C, the bent angle is approximately 55 degrees. In the accompanying parallel figure we see the same shaft 520, this time in a position D, with a bent angle near or at 90 degrees off normal. For each bent angle, we see that shaft 520 begins to bend at different positions depending at the angle of incidence at which the torqueing force will be applied. At position D, we see that a torqueing force is to be applied to a dental prosthetic 600 (shown in partial cross-sectional view).

Figure 1:
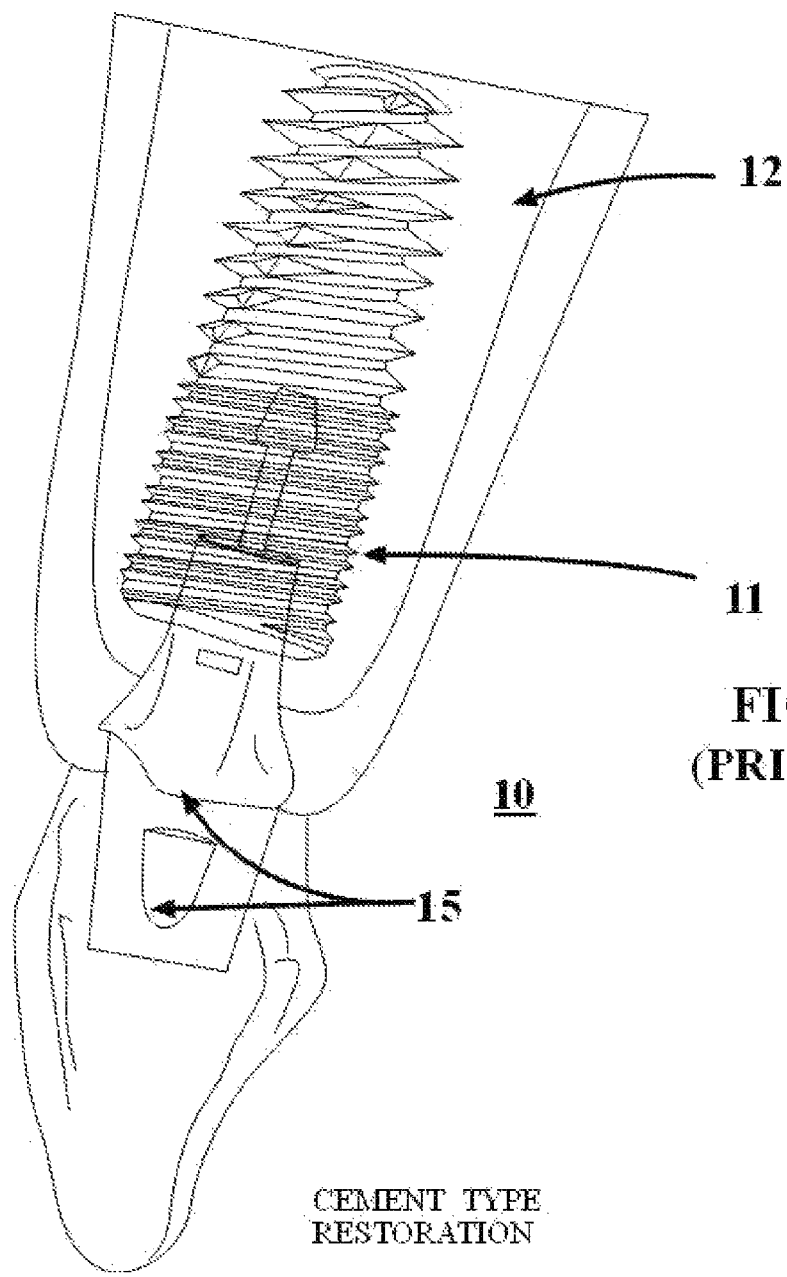
FIG. 1 is a cross-sectional view 10 of a dental implant 11 osseointegrated in jaw portion of a patient's mouth, and having a dental prosthetic shown fixed to dental implant using dental cement.
Figure 2A:
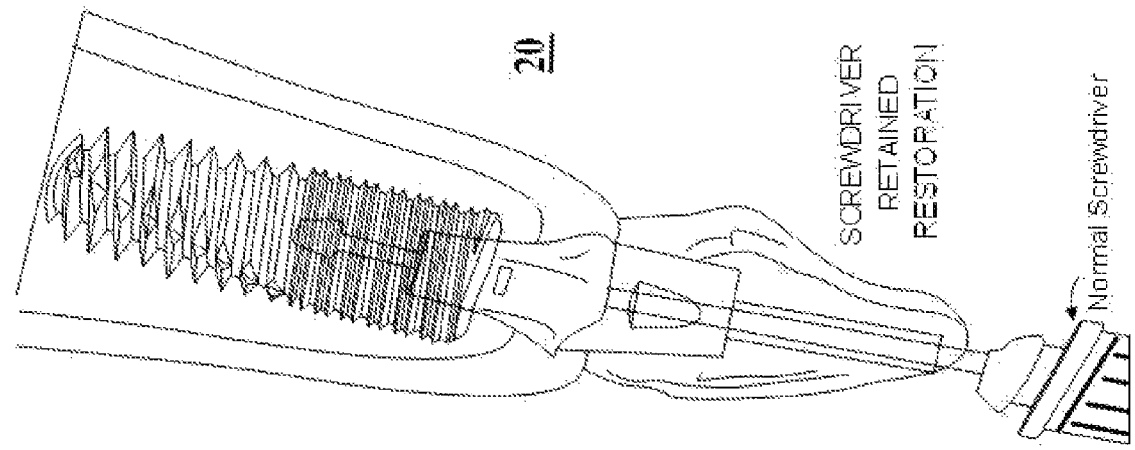
FIGS. 2A and 2B illustrate in cross-sectional view, a conventional screw-retained restoration approach, before screwing and during screwing, respectively.
Figure 2B:
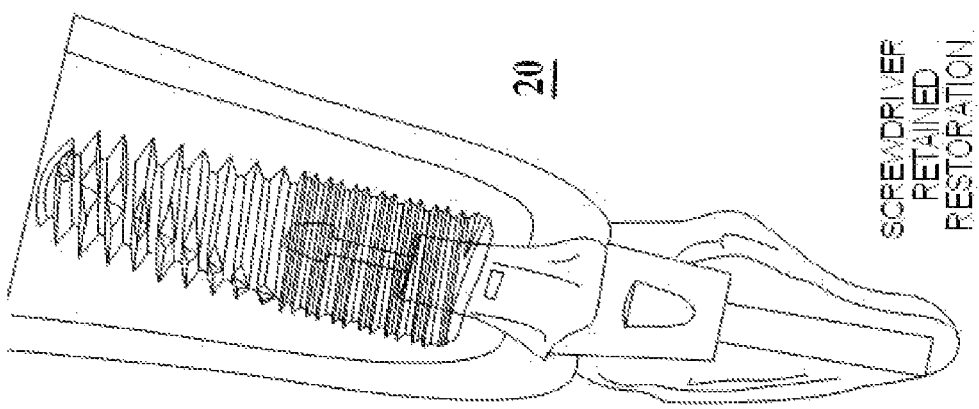
Figure 3B:
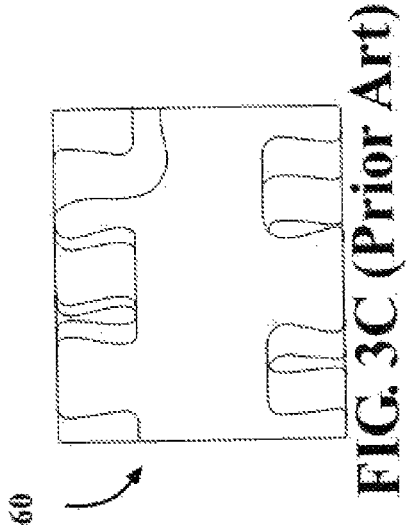
FIGS. 3A-3C are different perspective views of a prior art Straumann screwdriver.
Figure 3C:
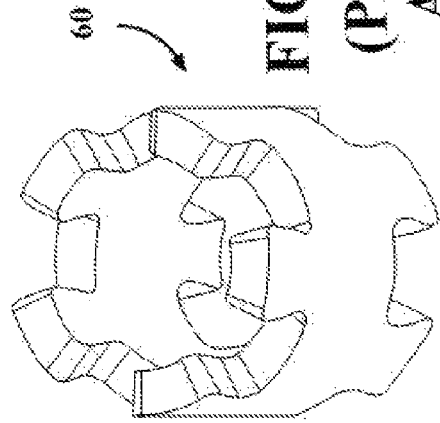
Figure 3A:
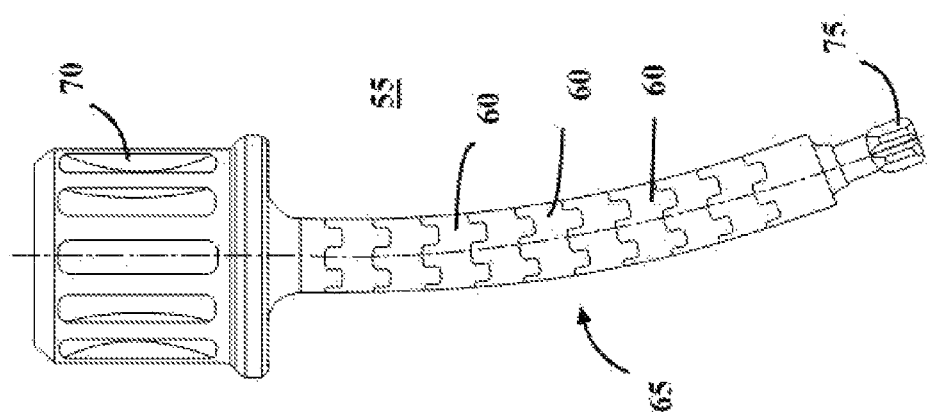
Figure 4A:
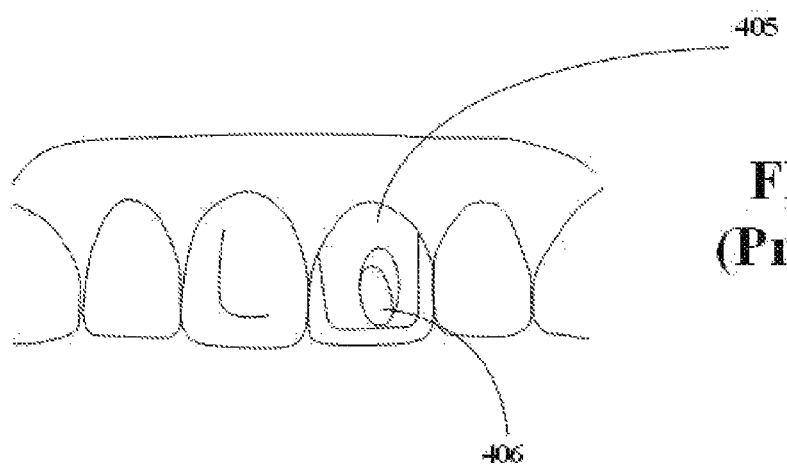
FIGS. 4A-4I illustrate the prior art Omnigrip approach.
Figure 4B:
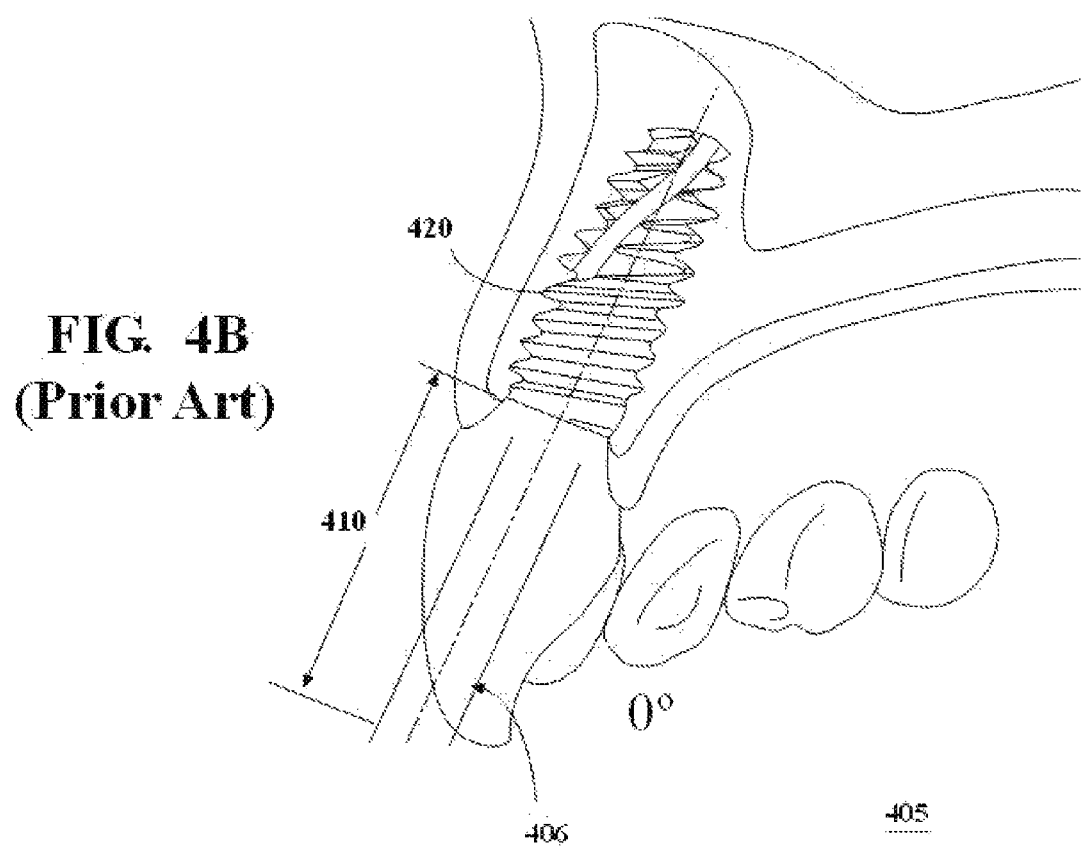
Figure 4C:
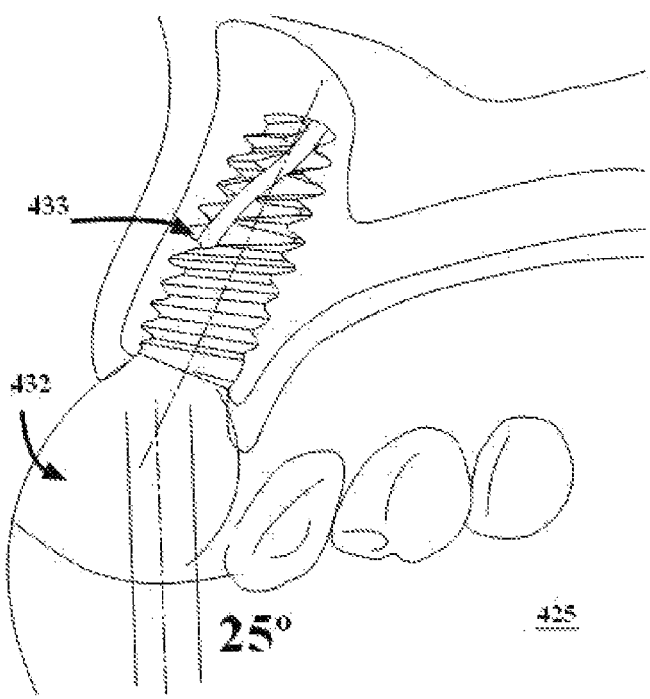
Figure 4D:
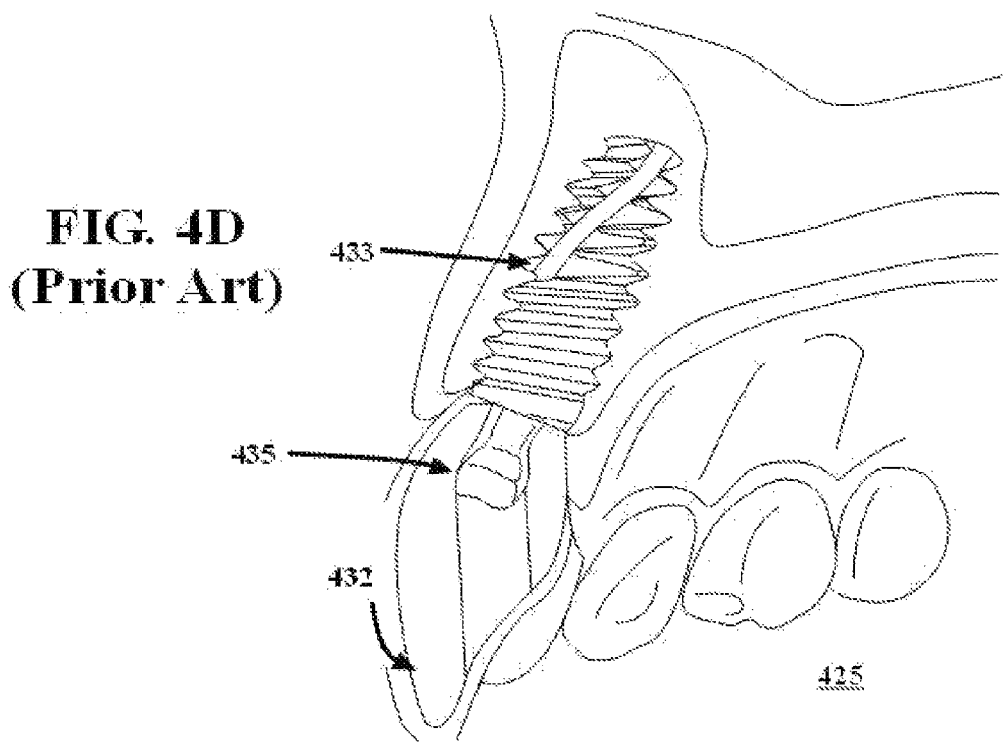
Figure 4E:
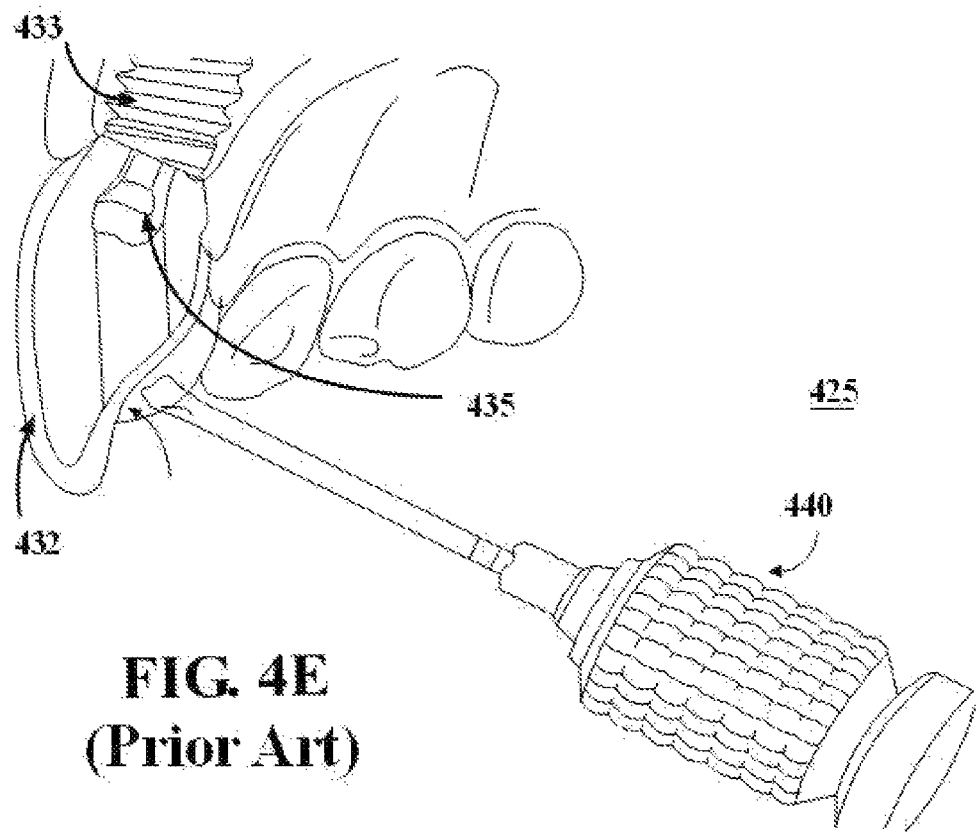
Figure 4F:
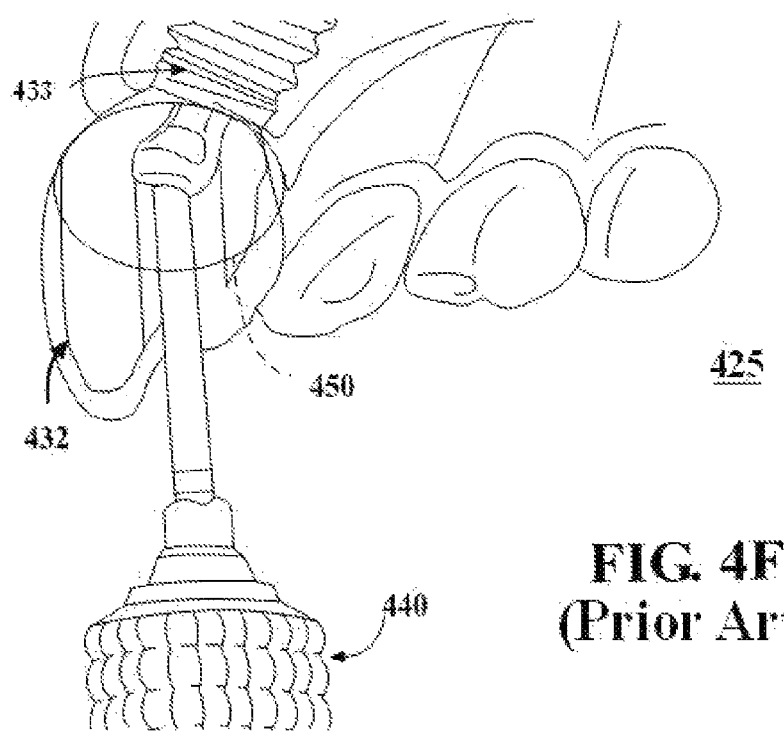
Figure 4G:
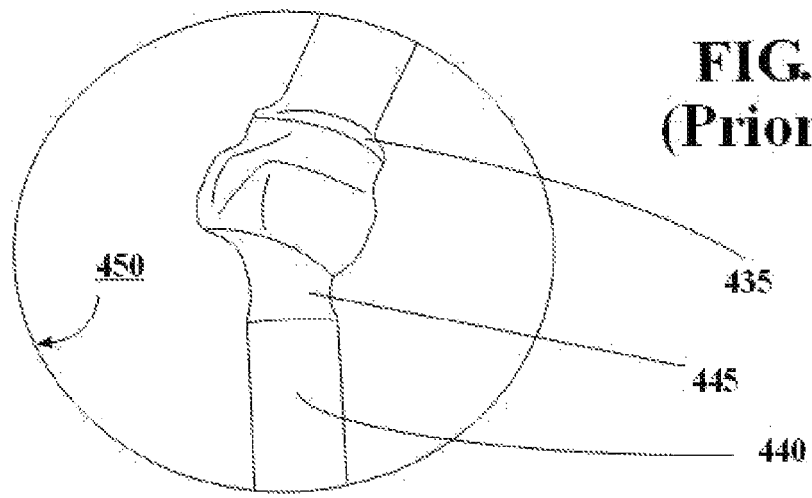
Figure 4H:
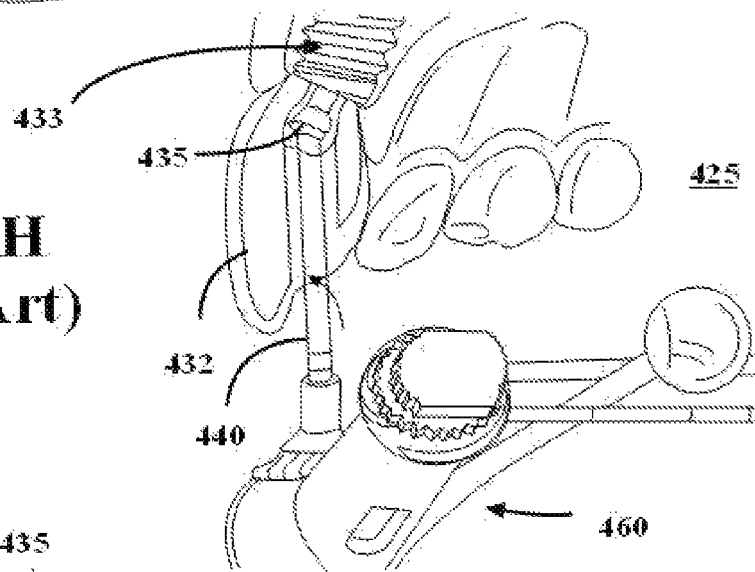
Figure 4I:
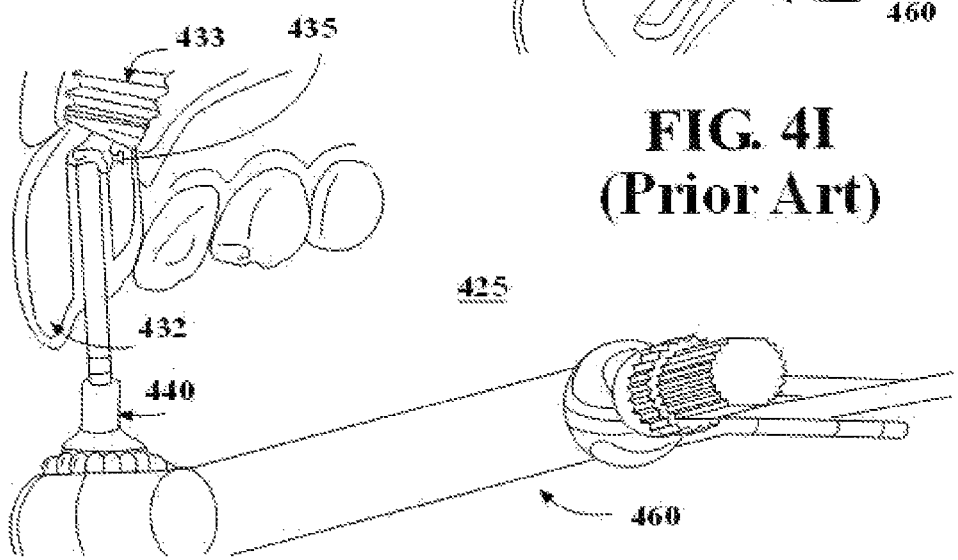

Dental prosthetic 600 includes an artificial tooth portion 610 into which has been fitted a conventional type screw retained type prosthetic abutment 620. Prosthetic abutment 620 includes a bore cavity 630 (preferably non-curved) configured to receive the screw (not shown) that's intended to secure dental prosthetic 600 to an abutting dental implant (not shown) for which it is designed, in the manner previously described above in connection with FIGS. 2A and 2B.

The artificial tooth portion 610 is unique in that it includes a "curved" bore cavity 640 which runs from the internal bore cavity 630 of abutment 620 to an eventual opening at the screw insertion end of dental prosthetic 600. While it is not necessary for bore cavity 640 to be curved, a curve may be desirable to allow the practitioner to screw dental prosthetic 600 to a dental implant for those teeth where additional bending elasticity is needed or desired to access during screwing and/or when, due to the nature of the tooth, it is easier to achieve a more aesthetic final result when filling in bore cavity 640 to complete the restoration.

The desired goal, again, is to provide a shaft capable of bending in an arch like manner along a central portion thereof but capable of maintaining a substantially linear curvature near and along drive tip end portion 550 to allow coupling same to a screw to be fitted in an abutment.

In an example scenario, the dental screwdriver is characterized by very high elasticity. Exposing the screwdriver to heating and/or applying subtle finger pressure helps with recovery to an original shape prior to bending. As such, the dental screwdriver is able to achieve a very high kink-resistance in concert with the ability to bend through torturous paths without experiencing strain localization and/or plastic deformation.

Figure 7:
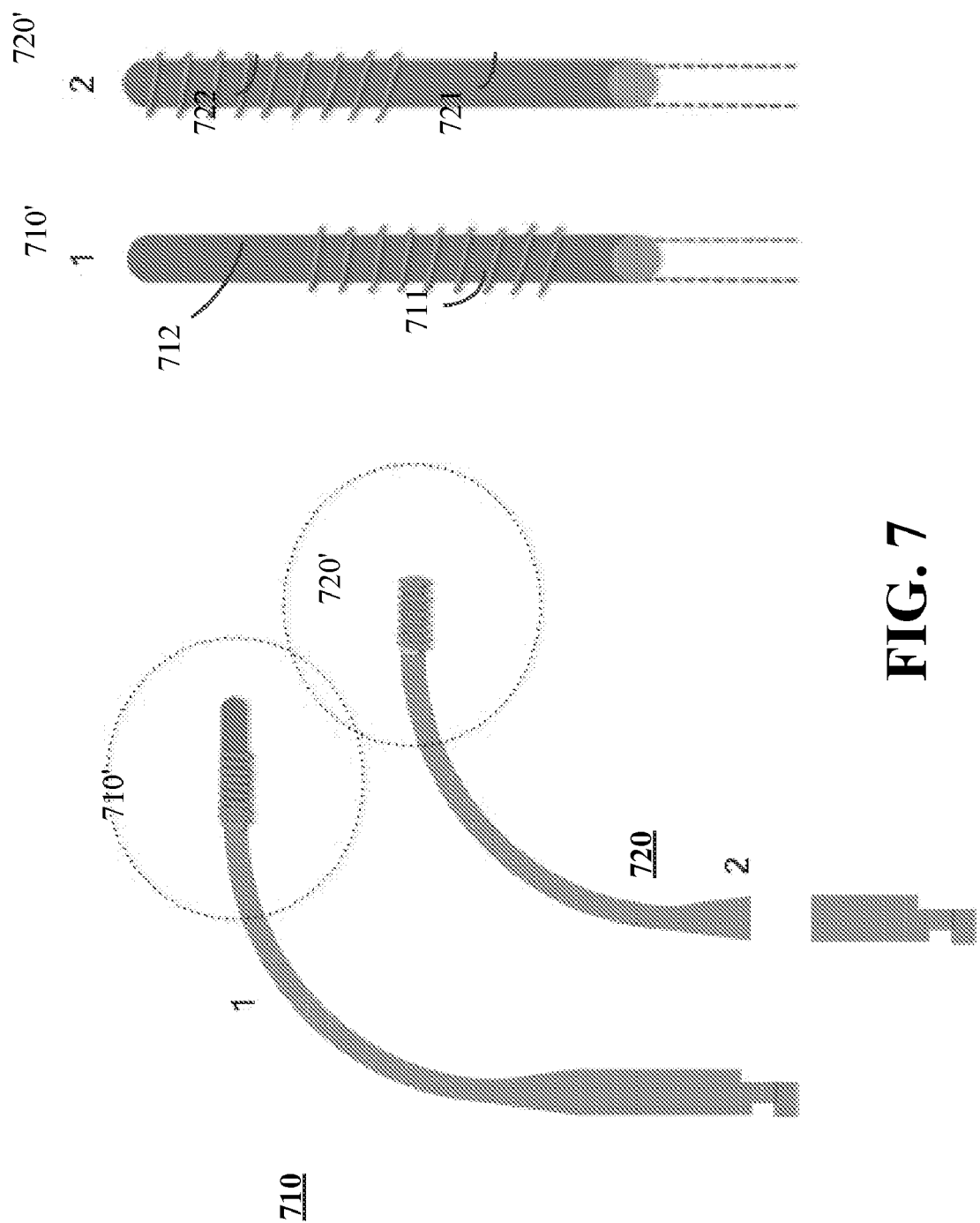
FIG. 7 shows an alternately shaped, smart alloy shaft in accordance with yet another exemplary embodiment.

FIG. 7 shows alternately shaped, smart alloy shafts in accordance with yet another exemplary embodiment. Shaft 710 is designed to function as an extractor tool in a Morse taper implant type configuration, while shaft 720 can be used as the activator tool to "activate" a Morse taper implant configuration.

Shaft 710 is characterized by a smart alloy distal end portion 710' which consists of a threaded portion 711 and a non-threaded portion 712. Portion 710' is a conventional extractor tool end design with the only difference being that distal end portion 710' is configured so as to bend into position during extraction, in the same way as has been described above in connection with the bendable screwdriver configurations. While Morse taper designs comprise both screw- and non-screw type implementations, the extractor tool itself provides the unlocking force needed to disengage (unlock) a prosthetic Morse tapered abutment (not shown) from the associated dental prosthetic.

Shaft 720, as explained, helps with activating the locking of the abutment to the prosthetic in a Morse taper design and also includes a smart alloy distal end portion 720', which in turn consists of a threaded portion 721 and a non-threaded portion 722 (with threaded portion 721 located at the complete distal end of shaft 720). Portion 720' is likewise a conventional activator tool end design with the only difference again being that distal end portion 720' is configured so as to bend into position during activation, in the same way as has been described above in connection with the bendable screwdriver configurations.

Technically speaking, smart alloy activator and extractor type shafts 720, 710 operate to couple and decouple, respectively, a Morse taper abutment to a fitted design dental prosthetic, and in this regard behave as dental screwdrivers as contemplated and defined herein. In the case of a Morse taper design of the type incorporating a screw in addition to (or as part of) the locking mechanism of the Morse taper configured design, shafts 710, 720 are designed to simultaneously impart the necessary torqueing of the available screw at the time of activation of the locking mechanism. If there is no screw, then the purpose of dental screwdriver with a shaft 720 is to engage the locking mechanism in the Morse taper configured implant alone. Likewise, the purpose of a dental screwdriver with a shaft 710 is to disengage the locking mechanism.

Figure 8:
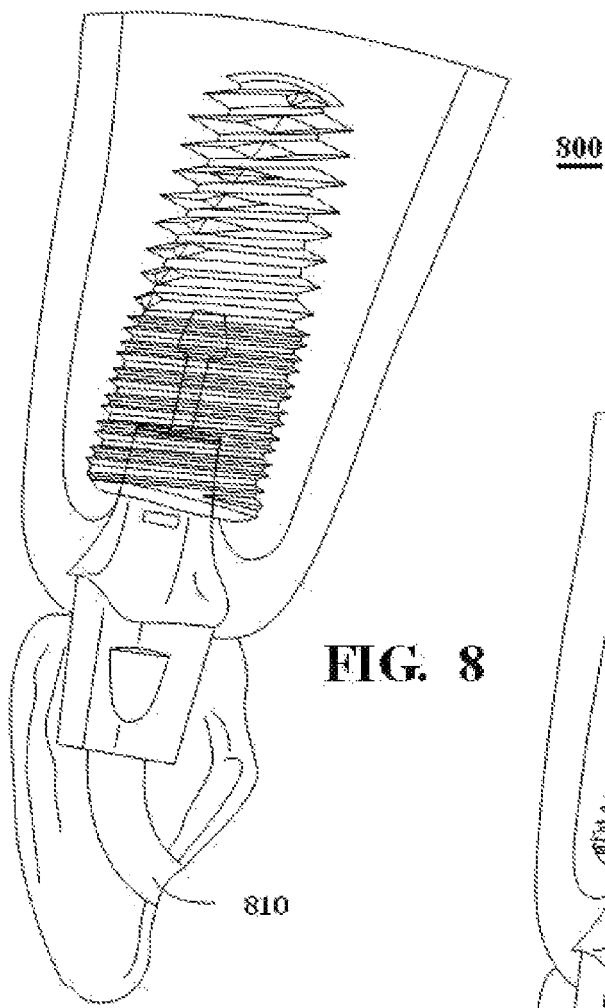
FIG. 8 shows a cross-sectional view of a screw-retained type restoration configured to be secured via a bore cavity that is at least partially curved.

FIG. 8 shows a cross-sectional view of a screw-retained type restoration 800 configured to be secured via a bore cavity 810 that is at least partially curved to allow a bendable screwdriver (not shown) with the proposed design to be inserted and the right amount of torque applied to the screw.

Figure 9:
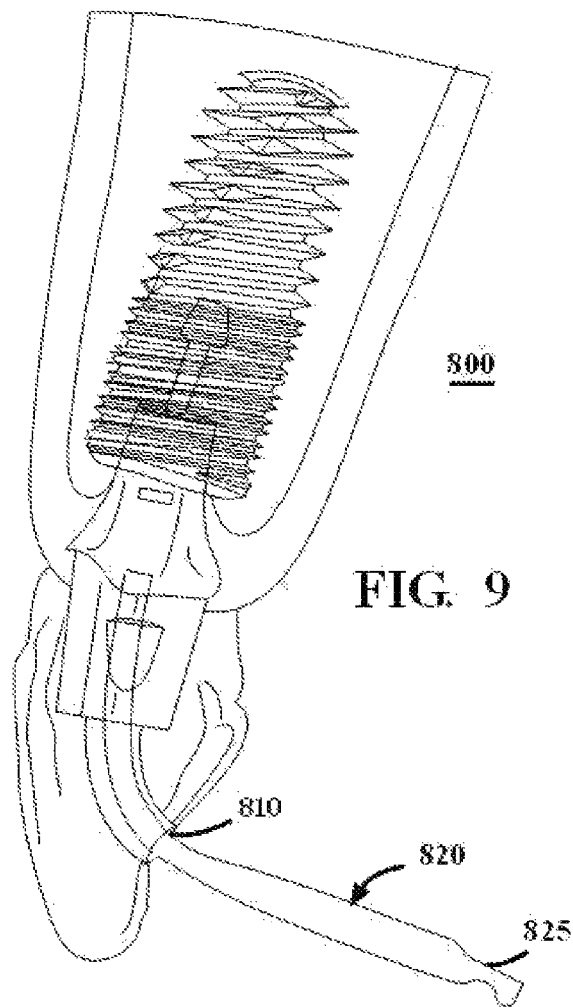
FIG. 9 shows a cross-sectional view which is a closer look of the screw retained type restoration in FIG. 8 with a bendable screwdriver shaft placed in the bore cavity during screw tightening action.

FIG. 9 shows a cross-sectional view which is a closer look of restoration 800—with a bendable screwdriver shaft 820 in position during screw tightening action. While the screwdriver axis at the point of insertion of the screw may appear bent, it is preferred that the vent be sized so that at the point where torque is applied the only force exerted on the screw at the point of contact is a radial (or torqueing type) force.

The screwdriver shaft and/or accompanying drive tips may be configured to match multiple restoration type specifications for added flexibility. Latch end 825 may be sized to have a universal head to accommodate different size or type handles, as well as torque-calibration and measuring type devices.

In yet another embodiment, the dental screwdriver is sized to have a very long shaft for flexibility in hard to reach places. The same shaft may alternatively include a telescopic portion disposed along a non-bendable, non-elastic portion of the shaft for even greater flexibility in use.

In yet a further embodiment, at least one of the shaft and the distal front end portion are magnetized to magnetically grip either a driver tip, the screw to be inserted, or both.

In yet a further embodiment there is further provided screws made of similar smart alloy material designed to conform to the specific shape of a vent or screw cavity when positioned for screwing to take advantage of the greater flexibility and reach the dental screwdriver proposed herein.

In yet a further embodiment, an electronic platform or stand-alone software tool may be provided to facilitate in the training or appropriate selection of a screwdriver having an elasticity, size, and/or dimension matching a restoration's optimum design specifications.

In one scenario, the platform is a smart-phone application providing appropriate visuals to help the practitioner select the appropriate tool, order replacement tips, learn about specific manufacturer torqueing specifications, and the like.

In yet a further embodiment, an electronic platform or stand-alone software tool, such as a smart phone application, may be provided to aid the practitioner in choosing an appropriately sized dental prosthetic of the type having a curved bore cavity to achieve an optimum aesthetic result and/or to achieve an optimum use of a bendable smart alloyed screwdriver during torqueing.

It should be appreciated that the use of a solid material instead of a segmented shafted design of Straumann or like prior art designs prevents having plural perpendicular forces applied on the abutment with at least one having a horizontal force vector capable of causing dislocation or fracture of an abutment.

By eliminating multiple non-angular forces, the torqueing force that is intentionally imparted by the practitioner is the only force being imparted on the screw head resulting in an optimum securing of a screw in position. At the same time, the level of skill and attention required by the practitioner is significantly reduced as are the risks of over- or under-torqueing and/or wrong torqueing, by the practitioner.

Because the shaft is not segmented, bending along different portions of the shaft is prevented. Uniform force distribution prevents future mechanical related fractures.

The proposed screwdriver provides improved resistance to repetitive strain excursions due to the homogenous material used.

Likewise, the improved shaft design results in bend uniformity which translates to improved overall fatigue resistance.

It should further be appreciated that the homogenous (non-segmented) nature of the proposed screwdriver implicitly provides much higher angulation without sacrificing height/length to achieve. This is due to a very large extent to the superior elasticity of smart alloy materials.

Also, superior hygiene is realized compared to the segmented shaft approach.

Most significantly, the present approach results in significant manufacturing costs improvements over both the Straumann type design as well as the Nobel Biocare design approach.

It should further be appreciated that a significant non-obvious affect of providing an arch-like bending section is that arches inherently have a natural starting point and a natural ending point. It is the space between these points that curves to absorb non-radial forces in a manner that do not get passed along to the distal front end portion where the torqueing affects must be singularly applied. This provides a unique and tremendous overall benefit in dental applications, but also in other applications where similar stresses exist.

Shaft and shaft tip specifications must allow for even and consistent shape transformation of the shaft, especially along the shaft bending-capable section, without the shaft exhibiting undue strain or kinking, and without distorting and/or adversely impacting the intended maximum desired torqueing force to be applied to a screw at the shaft tip end. In other words, the shaft should bend and rotate where it is supposed to bend and rotate to match the curvature of the channel about which it is being rotated but without preventing an even maximum torqueing force (measurable by a coupled torqueing tool) to be applied to the tip end during tightening. To achieve this, constituent materials from which the smart alloy is to be formed may need to be selected to meet desired optimum use parameters.

Smart alloys are comprised of crystal nanostructures that make non-destructive transformation possible. Further improvements may be realized by selecting tip ends and screw head dimensions that minimize natural wear and tear of the smart alloy, and/or change kink-resistance and stain deformation along the shaft. By altering the number of planes that the screwdriver tip engages (for example, providing a sixteen-faceted molecular structure), the smart alloy material from which the screwdriver is manufactured may exhibit stronger molecular compatibility resulting in increased resistance to breaking, wear or the like at the point of contact with screw, allowing at the same time hardening the head only. In another scenario, and for similar reasons, the screw is also made of smart alloy material.

These and other features and advantages of the present invention will be apparent from the description of exemplary embodiments provided herein.

These and other features and advantages of the present invention will be apparent from the description of exemplary embodiments provided herein.

The embodiments described above are intended to illustrate aspects of the invention and modifications, variants and equivalents such as would be readily apparent to the skilled person are encompassed within the scope of the invention such as defined, for example, by the claims.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments of the invention.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein

What is claimed is:

1. A dental screwdriver for use in a patient's mouth to securely fix a dental prosthetic to a dental implant, the dental screwdriver comprising:
   a non-segmented shaft that is sized and shaped to fit into
      a curved bore cavity of the dental prosthetic, the shaft including:
      a distal front end portion;
      a distal rear end portion opposite the distal front end portion and configured to couple to at least one of a handle portion and a torque measuring tool;
      an axial shaft portion disposed between the distal front end portion and the distal rear end portion, the axial shaft portion being made of a nickel titanium alloy and configured to elastically bend from an original shape to a bent shape along the axial shaft portion without imparting a bending action and torqueing forces along the distal front end portion and the distal rear end portion of the shaft when the shaft is fitted into the curved bore cavity of the dental prosthetic, the axial shaft portion being further configured to elastically return towards the original shape from the bent shape; and an integral drive tip disposed at the distal front end portion of the shaft and configured to drive a dental screw for securely fixing the dental prosthetic to the dental implant, wherein the integral drive tip and the distal front end portion of the shaft are made of nickel titanium with different material characteristics than that of the axial shaft portion.

2. The dental screwdriver of claim 1, wherein the dental screwdriver is uniquely weighted, sized and/or dimensioned to handle different torqueing functions, and/or configured to bend to a specific maximum angular arch without permanent deformation.

3. The dental screwdriver of claim 1, wherein the dental screwdriver is color coded to indicate screwdriver elasticity attributes.

4. The dental screwdriver of claim 1, wherein a substantially linear curvature is maintained near and along the distal front end portion when the axial shaft portion elastically bends from the original shape to the bent shape and elastically returns towards the original shape from the bent shape to allow coupling of the drive tip to the dental screw when the shaft is fitted into the curved bore cavity of the dental prosthetic.

5. The dental screwdriver of claim 1, wherein elasticity of the nickel titanium alloy of the axial shaft portion is characterized by maintaining a kink-resistance while bending through tortuous paths without experiencing strain localization and/or plastic deformation.

6. The dental screwdriver of claim 1, wherein the integral drive tip is designed to accommodate different manufacturer screw heads.

7. The dental screwdriver according to claim 1, wherein the distal front end portion is less elastic than the axial shaft portion.

8. The dental screwdriver according to claim 1, wherein the axial shaft portion has a continuous cross section.

9. The dental screwdriver according to claim 1, wherein the axial shaft portion has a solid core cross section.

10. The dental screwdriver according to claim 1, wherein the axial shaft portion is configured to elastically return to its original shape either in the absence of bending forces on the shaft or by applying heat or subtle finger pressure.

11. The dental screwdriver according to claim 1, wherein the axial shaft portion is axially homogenous.

12. The dental screwdriver of claim 1, wherein the integral drive tip is made of harder nickel titanium than the axial shaft portion.

13. The dental screwdriver of claim 1, wherein the integral drive tip is made of less bendable nickel titanium than the axial shaft portion.

14. The dental screwdriver of claim 1, wherein compared to the axial shaft portion, the distal rear end portion is made of either a non-smart alloy material, or of a smart alloy material of different elasticity, or of the same nickel titanium alloy but with different elasticity attributes along the shaft length.

15. The dental screwdriver of claim 1, wherein the distal front end portion of the shaft has a substantially constant outer diameter.

16. The dental screwdriver of claim 1, wherein the axial shaft portion is formed in one piece with both the distal front end portion and the integral drive tip.

17. A dental screwdriver for use in a patient's mouth to securely fix a dental prosthetic to a dental implant, the dental screwdriver comprising:

a non-segmented shaft configured to fit into a curved bore cavity of the dental prosthetic, the shaft having a first distal end portion, a second distal end portion disposed opposite the first distal end portion, a handle portion disposed at the second distal end portion, an axial shaft portion disposed between the first and second distal end portions, and a drive tip disposed at the first distal end portion for driving a fastener to securely fix the dental prosthetic to the dental implant;

wherein the axial shaft portion is made of a nickel titanium alloy and the drive tip and the first distal end portion are made of nickel titanium with different material characteristics than that of the axial shaft portion such that during use of the dental screwdriver, the axial shaft portion is configured to (i) elastically bend from an original shape to a bent shape along the axial shaft portion and (ii) elastically return towards the original shape from the bent shape without imparting a bending action and torqueing forces along the first distal end portion of the shaft when the shaft is fitted into the curved bore cavity of the dental prosthetic; and wherein compared to the axial shaft portion, the second distal end portion is made of either a non-smart alloy material, or of a smart alloy material of different elasticity, or of the same nickel titanium alloy but with different elasticity attributes along the shaft length; and wherein the axial shaft portion is further configured to elastically bend without imparting any bending action along the second distal end portion when the shaft is fitted into the curved bore cavity of the dental prosthetic.

18. The dental screwdriver of claim 17, wherein the first distal end portion has a substantially constant outer diameter.

19. The dental screwdriver of claim 17, wherein a substantially linear curvature is maintained near and along the first distal end portion when the axial shaft portion elastically bends from the original shape to the bent shape and elastically returns towards the original shape from the bent shape to allow coupling of the drive tip to the fastener when the shaft is fitted into the curved bore cavity of the dental prosthetic.

20. A dental screwdriver for use in a patient's mouth to securely fix a dental prosthetic to a dental implant using a dental screw, the dental screwdriver comprising:

a non-segmented shaft that is sized and shaped to fit into a curved bore cavity of the dental prosthetic, the shaft including:

a distal front end portion;

an integral screw drive tip disposed at the distal front end portion for driving the dental screw to securely fix the dental prosthetic to the dental implant;

a distal rear end portion opposite the distal front end portion and configured to couple to at least one of a handle portion and a torque measuring tool; and a bendable axial shaft portion formed in one piece with the distal front end portion, the distal rear end portion, and the drive tip, the bendable axial shaft portion being disposed between the distal front end portion and the distal rear end portion, the bendable axial shaft portion being made of a nickel titanium alloy and configured to elastically bend from an original shape to a bent shape along the bendable axial shaft portion without imparting a bending action and torqueing forces along the distal front end portion and the distal rear end portion of the shaft when the shaft is fitted into the curved bore cavity of the dental prosthetic and during driving of the dental screw by the drive tip to securely fix the dental prosthetic to the dental implant, and the bendable axial shaft portion being further configured to elastically return towards the original shape from the bent shape;

wherein the drive tip and the distal front end portion of the shaft are made of nickel titanium with different material characteristics than that of the bendable axial shaft portion; and wherein the distal front end portion is less elastic than the bendable axial shaft portion such that a substantially linear curvature is maintained near and along the distal front end portion when the bendable axial shaft portion elastically bends from the original shape to the bent shape and elastically returns towards the original shape from the bent shape to allow coupling of the drive tip to the dental screw when the shaft is fitted into the curved bore cavity of the dental prosthetic.

* * * * *